United States Patent
Gull et al.

[19]

[11] Patent Number: 6,138,674
[45] Date of Patent: Oct. 31, 2000

[54] ACTIVE TEMPERATURE AND HUMIDITY COMPENSATOR FOR ANESTHESIA MONITORING SYSTEMS

[75] Inventors: Kathleen Bergeron Gull, Sunnyvale, Calif.; William C. Hunt, Boulder, Colo.

[73] Assignee: Datex-Ohmeda, Inc., Tewksbury, Mass.

[21] Appl. No.: 08/951,894

[22] Filed: Oct. 16, 1997

[51] Int. Cl.[7] .................................................. A61M 16/00
[52] U.S. Cl. ................................ 128/204.21; 128/204.23
[58] Field of Search .......................... 128/204.21, 204.23, 128/205.23; 600/531, 532, 543

[56] References Cited

U.S. PATENT DOCUMENTS

| | | | |
|---|---|---|---|
| Re. 34,938 | 5/1995 | Serikov et al. ........................... | 128/691 |
| 3,799,149 | 3/1974 | Rummel et al. ......................... | 600/531 |
| 3,831,707 | 8/1974 | Takeuchi ................................. | 600/532 |
| 4,298,010 | 11/1981 | Eckstein et al. ......................... | 600/532 |
| 4,314,564 | 2/1982 | Albarda ................................... | 600/532 |
| 4,572,208 | 2/1986 | Cutler et al. ............................. | 600/531 |
| 4,648,714 | 3/1987 | Benner et al. ........................... | 356/301 |
| 4,707,336 | 11/1987 | Jones ....................................... | 422/84 |
| 4,753,245 | 6/1988 | Gedeon ................................... | 600/531 |
| 4,809,810 | 3/1989 | Elfman et al. ........................... | 600/532 |
| 4,914,720 | 4/1990 | Knodle et al. ........................... | 250/343 |
| 4,975,582 | 12/1990 | Mount et al. ............................ | 250/343 |
| 5,046,018 | 9/1991 | Flewelling et al. ...................... | 600/532 |
| 5,081,998 | 1/1992 | Yelderman et al. ..................... | 600/532 |
| 5,092,342 | 3/1992 | Hattendorff et al. .................... | 600/532 |
| 5,231,591 | 7/1993 | Flewelling et al. ...................... | 600/532 |
| 5,261,415 | 11/1993 | Dussault .................................. | 600/532 |
| 5,296,706 | 3/1994 | Braig et al. .............................. | 600/532 |
| 5,340,987 | 8/1994 | Eckles et al. ............................ | 250/345 |
| 5,436,457 | 7/1995 | Tomita .................................... | 250/343 |
| 5,444,249 | 8/1995 | Wong ....................................... | 250/343 |
| 5,464,982 | 11/1995 | Drucker et al. .......................... | 250/343 |
| 5,468,961 | 11/1995 | Gradon et al. ........................... | 250/343 |
| 5,468,962 | 11/1995 | Ohishi et al. ............................ | 250/343 |
| 5,531,225 | 7/1996 | Nawata et al. ........................... | 600/532 |
| 5,800,360 | 9/1998 | Kisner et al. ............................ | 600/532 |

*Primary Examiner*—Aaron J. Lewis
*Attorney, Agent, or Firm*—Marsh Fischmann & Breyfogle, LLP

[57] ABSTRACT

The humidity and/or temperature of a gas sample is monitored so that these system parameters can be accounted and/or actively monitored and controlled. In one embodiment, a gas analyzer system (10) includes an input flowline (12) for receiving a sample stream from a patient respiratory circuit via a patient input module (14), an analyzer instrument (16) for obtaining composition information regarding the gas sample, a humidity sensor module (18) containing a temperature sensor (40) and a humidity sensor (42), and a vacuum pump (22) for drawing the gas sample through the analyzer system (10). A processor (28) receives information from the analyzer instrument (16) and the humidity sensor module (18) and determines composition information regarding the gas sample based on such inputs. The analyzer system (10) thereby allows for improved composition measurements and for monitoring the humidity of the gas sample to stay within specifications or preferred operating ranges of certain analyzer instruments.

19 Claims, 3 Drawing Sheets

ACTIVE TEMPERATURE AND HUMIDITY COMPENSATOR FOR ANESTHESIA MONITORING SYSTEMS

FIELD OF THE INVENTION

The present invention relates in general to gas analyzers and, in particular, to gas analyzers that measure humidity and/or temperature in gas samples so that the values of these parameters can be taken into account in determining gas composition or controlling the relative humidity of the gas sample at critical components of the analyzer. The invention is particularly applicable to monitoring administration of anesthesia during a medical procedure.

BACKGROUND OF THE INVENTION

Gas analyzers are used in medical and industrial environments to analyze the composition of gas samples, e.g., to determine the presence and/or concentration of components of interest in such samples. In the medical environment, gas analyzers are used, for example, to monitor the administration of anesthesia during medical procedures. The components of interest that are monitored in such applications may include anesthetic agents such as isoflurane, enflurane, halothane, desflurane and sevoflurane and respiratory gases such carbon dioxide. Various other therapeutic gases may also be monitored depending on the application. The gas analyzer may operate on gas within the main patient respiratory stream, or on a side stream diverted from the main respiratory stream.

Various types of gas analyzers are used in connection with monitoring administration of anesthesia including spectrographic gas analyzers, Raman scattering gas analyzers, and of anesthesia including spectrographic gas analyzers, Raman scattering gas analyzers, and electrochemical gas analyzers. Spectrographic gas analyzers generally include an illumination source and an illumination detector. Illumination from the source is transmitted through the gas sample and is measured by the detector. Composition information is determined based on known transmissions/absorption characteristics of the components of interest. Raman scattering spectrometers involve transmitting coherent illumination through the gas sample and detecting scattered illumination. Composition information is determined based on known scattering characteristics of the compositions of interest. Electrochemical gas analyzers involve contacting the sample gas with an electrochemical cell or cells and measuring resulting electrical signals. Composition information is determined based on known electrochemical characteristics of the components of interest.

The processing to determine composition information based on analyzer output typically involves calculating a value related to the analyzer output and determining composition information corresponding to the value based on a database of empirically derived information concerning the components of interest. In order to ensure accuracy, certain system parameters such as illumination source intensity or detector temperature may be monitored and changes in such system parameters may be accounted for in making composition determinations. Certain sample gas parameters such as pressure may also be taken into consideration. Other parameters, such as humidity, have generally not been taken into consideration in making composition determinations or designers/operators have attempted to control or limit values of such parameters without active monitoring through the use of filters, humidifiers or the like. Such attempts to control or limit humidity in connection with a patient respiratory stream have proved problematic and have not been entirely successful.

SUMMARY OF THE INVENTION

The gas analyzer system of the present invention senses a humidity and/or temperature in a gas sample so that these system parameters can be accounted for and/or actively monitored and controlled. The measurements can be employed by a processor to compensate for variations in humidity or temperature in making composition determinations and otherwise provide useful information concerning these parameters. The invention thereby allows for improved gas analyzer operation and accuracy.

According to one aspect of the present invention, a novel sensor module is pneumatically interposed in a gas sample flowline of the gas analyzer. The module includes a housing that is sealed from the ambient environment, a sample inlet for receiving a sample stream from the analyzer flowline into the sealed housing, and a sample outlet for returning the sample stream from the sealed housing to the analyzer flowline. A humidity sensor and, preferably, a temperature sensor are disposed within the sealed housing to measure the humidity and, if desired, the temperature of the sample stream. The module further includes an electrical interface for use in transmitting signals from the sensor(s) to a processor of the gas analyzer. The electrical interface may include, for example, leads extending from the sensors through sealed openings in the housing to a printed circuit board mounted on the housing. In this manner, humidity and/or temperature readings can be continuously or periodically reported to the processor during a measurement period, e.g., during a medical procedure. This information can be used, for example, to compensate for changes in humidity and temperature in making sample stream composition calculations, or to monitor relative humidity levels which may affect the performance or lifespan of other analyzer components.

According to another aspect of the present invention, humidity and/or temperature readings are used to monitor the composition of a patient's respiratory stream during a medical procedure. The corresponding gas analyzer system includes a patient input for receiving a gas sample from a patient respiratory stream, a gas exhaust for exhausting the sample (e.g., returning the sample to the respiratory stream or exhausting to the ambient environment after proper treatment), a gas analyzer instrument located on an analyzer system flowline between the gas inlet and gas exhaust for obtaining composition information regarding the gas sample, a humidity sensor module, including a humidity and/or temperature sensor, located on the analyzer flowline between the gas input and gas exhaust, and a processor for receiving information from the gas analyzer instrument and the humidity sensor module and determining composition information regarding the patient sample stream based on such information. The humidity sensor module is preferably located downstream from the gas analyzer instrument. The gas analyzer instrument may be, for example, a spectrographic analyzer, a Raman analyzer or an electrochemical cell based analyzer. The gas analyzer system can thus take the humidity and temperature of the patient sample stream into account in making concentration determinations regarding the patient sample stream, and can be used to maintain the relative humidity of the stream at desired levels.

BRIEF DESCRIPTION OF DRAWINGS

For a more complete understanding of the present invention and further advantages thereof, reference is now made to the following detailed description taken in conjunction with the drawings in which.

DETAILED DESCRIPTION OF THE INVENTION

In the following description, the invention is set forth in the context of a gas analyzer system for use in monitoring the administration of anesthesia during a medical procedure. As will be readily appreciated, significant humidity may be present in the patient respiratory stream. Such humidity can affect values measured by the gas analyzer system. Humidity can also affect operation of certain analyzer components. Accordingly, the active humidity and temperature monitoring system is particularly advantageous with respect to medical environments such as the anesthesia monitoring environment as described below. However, it would be appreciated that certain aspects of the present invention are more generally applicable to a variety of gas analyzer environments and applications.

Figure 1:
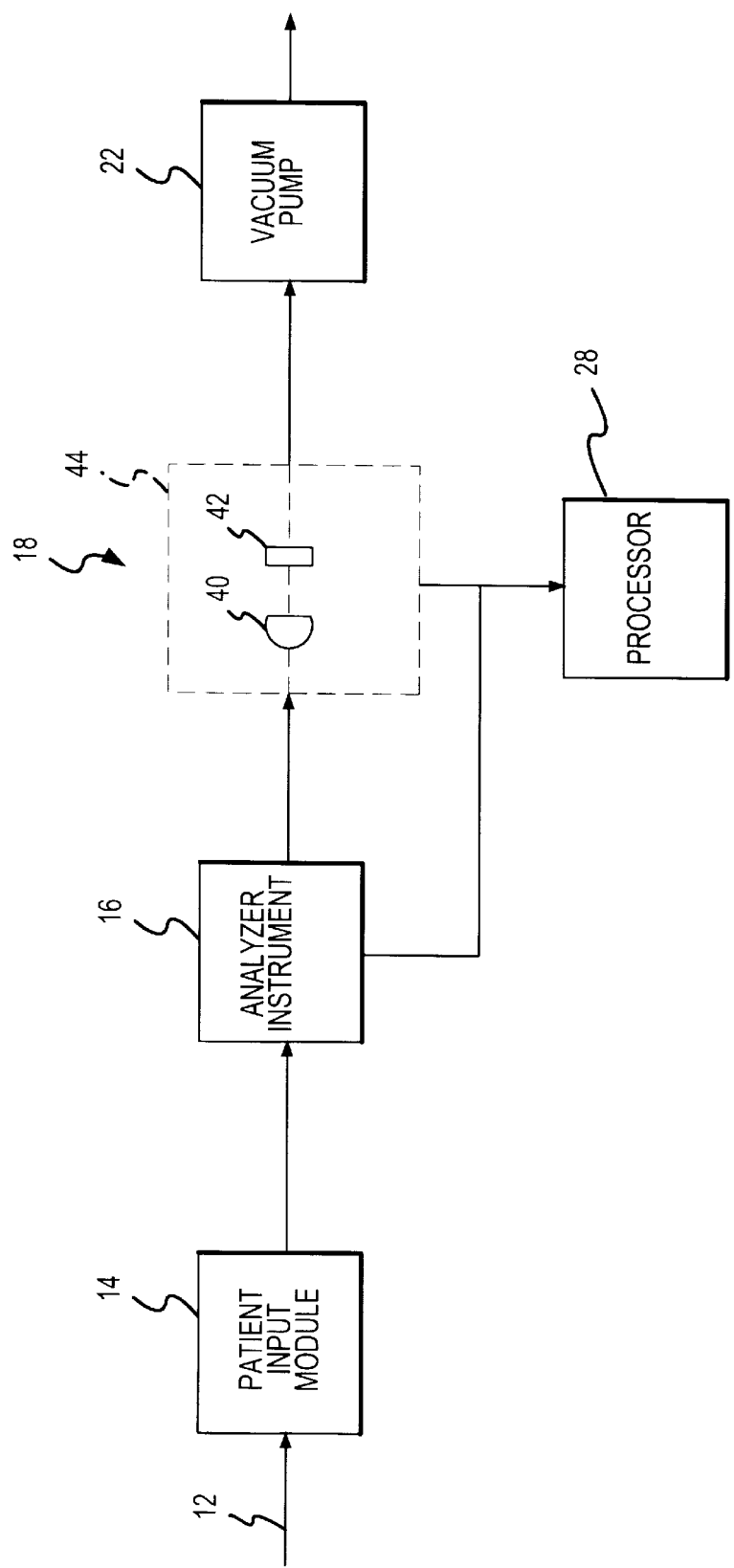
FIG. 1 is a schematic diagram of a gas analyzer system according to the present invention.

Referring to FIG. 1, a general schematic diagram of a gas analyzer system 10 according to the present invention is shown. The various connecting lines in the illustrated embodiment represent conduits that define an overall flowline through the system 10. Generally, the illustrated gas analyzer system 10 includes: an input flowline 12 for receiving a sample stream from a patient respiratory circuit via patient input module 14; an analyzer instrument 16 for obtaining composition information regarding the gas sample (in this case, a sample stream); a humidity sensor module 18, for measuring the temperature and humidity of the gas sample; and a vacuum pump 22 for drawing the gas sample through the gas analyzer system 10. The gas analyzer system 10 further includes a processor 28 such as a computer for, among other things, receiving information from the analyzer instrument 16 and the humidity sensor module 18 and determining composition information regarding the gas sample based on such input. In addition to the illustrated components, analyzer system 10 may also include an autozeroing subsystem for periodically zeroing the analyzer instrument 16, a system purging subsystem for use in dislodging any flaw obstructions in the analyzer system 10 and various other components that are omitted from the drawings for purposes of clarity.

The analyzer system 10 can be inserted directly into the main patient respiratory line or can operate within a side stream diverted from the main line. In either case, the patient input module 14 receives gases of the patient respiratory stream and removes mucous or particulates from the stream that could harm the gas analyzer system 10. From the patient input module 14, the gas stream passes to the analyzer instrument 16.

Various types of analyzer instruments may be employed in accordance with the present invention. Examples include spectrographic gas analyzer instruments, Raman scattering gas analyzer instruments, and electrochemical cell based gas analyzer instruments. In the illustrated embodiment, the analyzer instrument 16 is a spectrographic gas analyzer that includes an array of illumination detector elements associated with a linear variable filter such that the detector elements provide intensity readings for a number of wavelengths within a selected spectral range. For example, the analyzer instrument 16 may include 70 to 80 detector elements providing readings distributed over the 4 to 12 micron spectral range. The analyzer instrument 16 thus provides output signals to the processor 28 that define a spectrum of transmitted intensities for use in determining the composition of the sample gas. The analyzer instrument may further provide reference gas measurements for calibration purposes. The sample gas and reference gas measurements can be obtained periodically, for example, at a rate of 20 cycles per second. The processor may further receive pressure transducer readings indicative of absolute pressure of the stream. As will be appreciated, such pressure readings are relevant to determining concentration information regarding components of the gas sample based on the instrument output.

Figure 2:
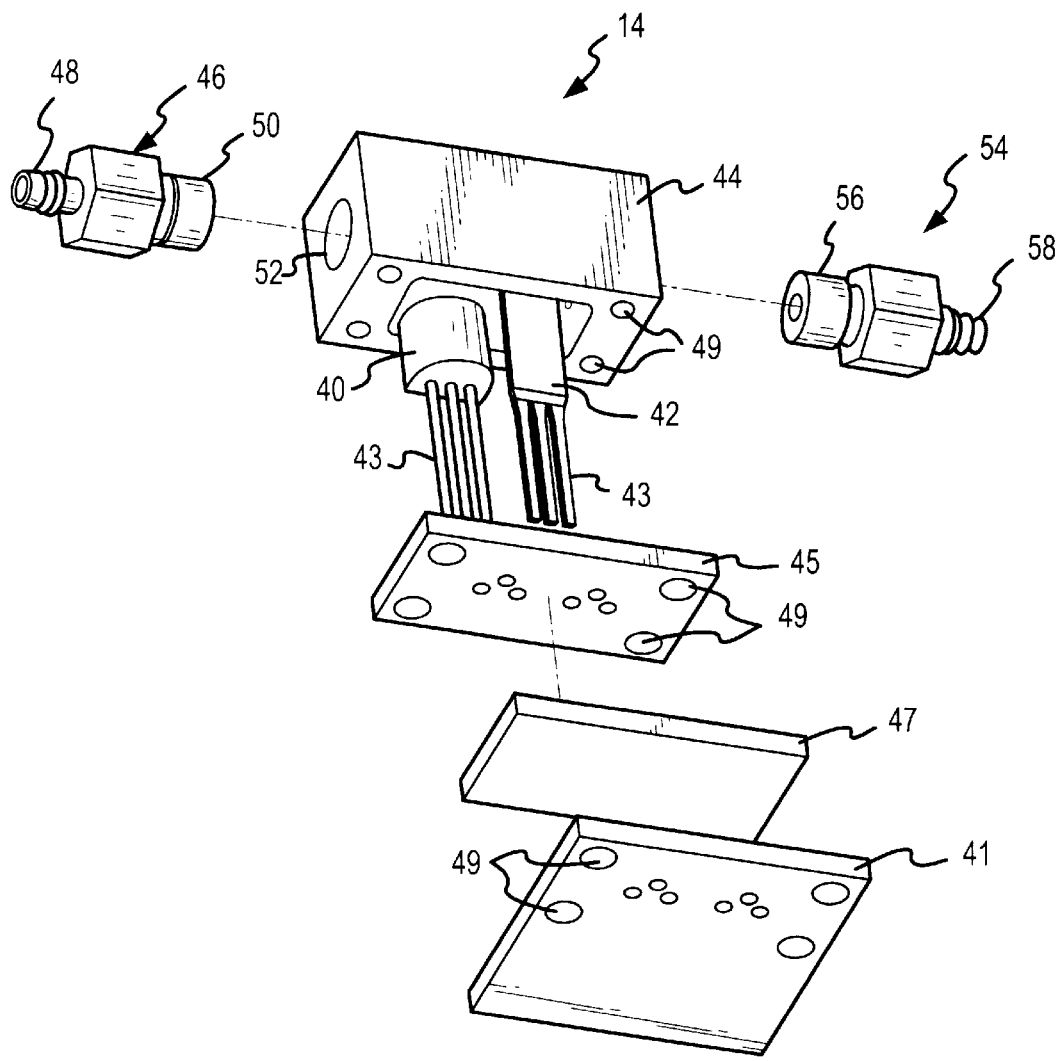
FIG. 2 is an exploded perspective view of a humidity sensor module of the gas analyzer system of FIG. 1.

Details of the humidity sensor module are shown in the exploded perspective view of FIG. 2. The module includes a temperature sensor 40 and a humidity sensor 42 located within a housing 44. Any suitable temperature and humidity sensors may be employed. The illustrated temperature sensor is a solid state temperature sensor manufactured by Analog Devices. The illustrated humidity sensor is a capacitance sensor with conditioning circuitry sensor manufactured by HyCal. The sample gas is introduced into the housing 44 via inlet adapter 46. The adapter 46 includes a first end plug 48 for mating with the analyzer flow line and a second end plug 50 for mating with an inlet opening 52 provided in a side wall of the housing 44. The end plugs 48 and 50 are dimensioned to provide sealed engagements with the flowline and opening 52 respectively. The sample gas exits the chamber via exhaust adapter 54. The exhaust adapter includes a first end plug 56 for mating with an opening (not shown) provided in a side wall of housing 44 and a second end plug 58 for interfacing with an analyzer flowline. Again, the end plugs 56 and 58 provide sealed engagements with respect to the housing 44 and flowline respectively.

The temperature sensor 40 and humidity sensor 42 provide electrical signals indicative of the temperature and humidity, respectively, in the sample stream. These signals are communicated to a printed circuit board 41 via leads 43. The leads 43 extend through openings in housing cover 47 and gasket 45. An o-ring(s) or the like may be used in place of gasket 45 to provide seal at thee cover/housing interface. The printed circuit board 41, cover 45, gasket 47 and housing 44 can be connected by screws or other fasteners inserted through openings 49.

The output from the humidity sensor module 18 is transmitted to the processor 28 which may use the humidity and temperature information in various ways. First, the temperature and humidity information can be used in making concentration determinations, e.g., determining the concentrations of various components of interest such anesthetic agents and respiratory gas components. In this regard, the effect of humidity and temperature on concentration measurements can be determined empirically and stored in a data base associated with the processor 28. The empirical data can be obtained by measuring known samples under known conditions using the analyzer instrument 16. The temperature and humidity information may also be used to actively monitor sample gas conditions and control such conditions to stay within preferred operating ranges. For example, the specifications for certain common analyzer components may require operation at a relative humidity between 15 and 90%. The temperature and humidity information provides a feedback relevant to determining relative humidity. This feedback can be used in operating conventional humidifier or filtering components so as to control the relative humidity of the gas sample.

Figure 3:
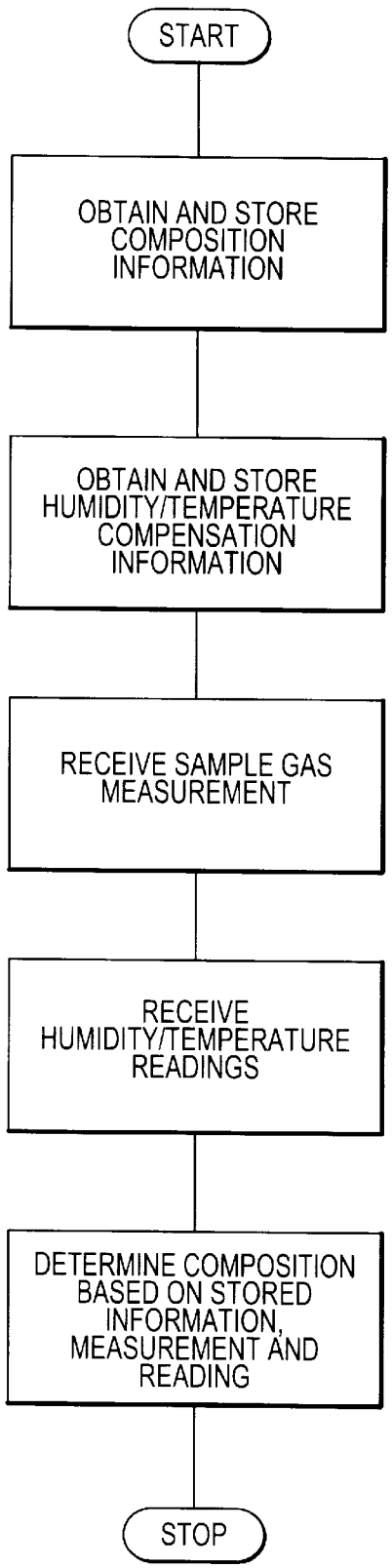
FIG. 3 is a flow chart of a processor implemented by the processor of the system of FIG. 1.

A process implemented by the processor 28 of the gas analyzer system 10 can be summarized by reference to the flow chart of FIG. 3. The process is initiated by obtaining (100) and storing composition information relating analyzer measurements to corresponding sample gas compositions. Such information can be derived theoretically based on known properties of the gaseous components of interest, or empirically by obtaining measurements for gases of known composition. Various algorithms and vectors may be employed to process the raw detector data so as to determine concentration on a component-by-component basis. Similarly, the processor obtains (110) and stores theoretically or empirically derived humidity/temperature compensation information relating temperature/humidity readings to appropriate composition compensation factors.

Once such information is obtained and stored, the gas analyzer system 10 may be operated such that the processor 28 receives (120) a sample gas measurement from the analyzer instrument 16. The nature of such information will vary depending on the specifics of the instrument. For example, the information may be based on illumination transmission/absorption characteristics, illumination scattering characteristics or electrochemical characteristics of the sample gas. In the case of a spectrographic gas analyzer, the information may take the form of received intensity measurements of various wavelengths or wavelength ranges of a selected spectrum. Such information may be obtained, for example, periodically during a medical procedure.

The processor 28 also receives (130) periodic temperature/humidity readings from the sensor module. Such readings are not necessarily obtained at the same times or frequencies as the detector instrument measurements and, in practice, can probably be taken less frequently as temperature and humidity are expected to vary relatively slowly. The processor 28 then determines (140) the sample gas composition based on the stored composition information, the stored humidity/temperature information, the sample gas measurement and corresponding temperature/humidity reading, thereby facilitating accurate composition determinations despite variations in sample gas humidity and temperature.

While various implementations of the present invention have been described in detail, it is apparent that further modifications and adaptions of the invention will occur to those skilled in the art. However, it is to be expressly understood that such modifications and adaptions are within the spirit and scope of the present invention.

What is claimed is:

1. A respiratory gas analyzer, comprising:
    a flow input for receiving a gas sample of a patient's respiratory stream;
    first analyzer means, for performing a first analysis of said gas sample to obtain composition information regarding a composition of said sample;
    second analyzer means, interconnected to said flow input to receive said gas sample, for performing a second analysis of said gas to obtain humidity information regarding a humidity of said gas sample, said second analyzer means comprising a humidity sensor disposed within a sealed housing a sample inlet for receiving said gas sample into said sealed housing, and a sample outlet for discharging said gas sample from said sealed housing, wherein each of said sample inlet and sample outlet comprises an adapter for sealingly engaging an opening of said housing at one end thereof and sealingly engaging a gas conduit at another end thereof; and
    processor means, for receiving said composition information and said humidity information and determining a composition of said gas sample based on said received information.

2. An analyzer as set forth in claim 1, wherein said flow input comprises a series of conduits for conveying said gas sample through said analyzer.

3. A gas analyzer as set forth in claim 1, wherein said first analyzer means comprises a spectrographic instrument for obtaining said composition information by measuring illumination transmitted through said gas sample.

4. A gas analyzer as set forth in claim 1, wherein said first analyzer means comprises an instrument for obtaining said composition information on the basis of illumination scattered by said gas sample.

5. A gas analyzer as set forth in claim 1, wherein said first analyzer means comprises an electrochemical cell for obtaining said composition information based on an electrochemical analysis of said gas sample.

6. A gas analyzer as set forth in claim 1, wherein said humidity sensor is mounted on said flow line.

7. A gas analyzer as set forth in claim 1, wherein said second analyzer means comprises a temperature sensor mounted on said flow line.

8. A gas analyzer set forth in claim 1, wherein said second analyzer means is mounted on said flow line downstream from said first analyzer means.

9. A gas analyzer as set forth in claim 1, wherein said second analyzer means comprises a temperature sensor disposed within said housing.

10. A gas analyzer as set forth in claim 1, wherein said processor means comprises means for determining concentration information for at least one component of interest of said sample gas based on said composition information and said humidity information.

11. A sensor module for use in a gas analyzer that includes an analyzer flowline for conveying a gas sample under analysis, said sensor module comprising:
    a housing that is sealed from the ambient environment;
    a sample inlet for receiving said gas sample from the analyzer flowline into the sealed housing;
    a sample outlet for returning said gas sample from said sealed housing to the analyzer flowline wherein each of said sample inlet and said sample outlet comprises an adapter for sealingly engaging an opening of said housing at one end thereof and sealingly engaging said analyzer flowline at another end thereof;
    a humidity sensor disposed within said sealed housing for measuring a humidity of said gas sample and providing electrical signals indicative of said measured humidity; and
    an electrical interface for use in transmitting said electrical signals from said humidity sensor to a processor of said gas analyzer.

12. A sensor module as set forth in claim 11, wherein said electrical interface comprises an electrical lead extending from said humidity sensor.

13. A sensor module as set forth in claim 11, wherein said electrical interface comprises a circuit board mounted on said housing and is electrically interconnected to said humidity sensor.

14. A sensor module as set forth in claim 11, further comprising a temperature sensor disposed within said housing.

15. A sensor module as set forth in claim 14, wherein said temperature sensor is disposed upstream from said humidity sensor relative to a flow direction of said analyzer flowline.

16. A gas analyzer comprising:

a flow input for receiving a gas sample to be analyzed;

an analyzer instrument for obtaining composition information regarding a composition of said gas sample;

a sensor module including a sealed module housing for receiving said gas sample, a temperature sensor disposed in said sealed housing for providing temperature information regarding a temperature of said gas sample, and a humidity sensor disposed in said sealed housing for providing humidity information regarding a humidity of said gas sample, wherein said temperature sensor is disposed upstream from said humidity sensor relative to a flow direction of said flow input; and a processor for receiving said composition information, said temperature information, and said humidity information and determining said composition of said gas sample based on said composition, temperature, and humidity information.

17. A gas analyzer as set forth in claim 16, wherein said analyzer instrument comprises a spectrographic gas analyzer instrument.

18. A gas analyzer as set forth in claim 16, further comprising a printed circuit board mounted on said sensor module for providing an electrical interface to said temperature sensor and said humidity sensor.

19. A sensor module for use in a gas analyzer that includes an analyzer flowline for conveying a gas sample under analysis, said sensor module comprising:

a housing that is sealed from the ambient environment;

a sample inlet for receiving said gas sample from the analyzer flowline into the sealed housing;

a sample outlet for returning said gas sample from said sealed housing to the analyzer flowline;

a temperature sensor disposed within said housing;

a humidity sensor disposed within said sealed housing for measuring a humidity of said gas sample and providing electrical signals indicative of said measured humidity, wherein said temperature sensor is disposed upstream from said humidity sensor relative to a flow direction of said analyzer flowline; and an electrical interface for use in transmitting said electrical signals from said humidity sensor to a processor of said gas analyzer.

* * * * *